United States Patent [19]

Miracca et al.

[11] Patent Number: 5,446,224

[45] Date of Patent: * Aug. 29, 1995

[54] INTEGRATED PROCESS FOR PRODUCING ISO-BUTENE AND ALKYL TERT-BUTYL ETHERS

[75] Inventors: Ivano Miracca, Lodi; Giorgio Fusco, Milan, both of Italy

[73] Assignee: Snamprotetti S.p.A., Milan, Italy

[*] Notice: The portion of the term of this patent subsequent to Oct. 19, 2010 has been disclaimed.

[21] Appl. No.: 46,954

[22] Filed: Apr. 16, 1993

Related U.S. Application Data

[63] Continuation of Ser. No. 787,790, Nov. 4, 1991, Pat. No. 5,254,764.

[30] Foreign Application Priority Data

Feb. 28, 1991 [IT] Italy ............................. MI91A0519

[51] Int. Cl.$^6$ ..................... C07C 5/03; C07C 41/06
[52] U.S. Cl. ...................... 585/324; 585/310; 585/654; 568/697
[58] Field of Search ............. 585/324, 654, 655, 310, 585/809; 568/697

[56] References Cited

U.S. PATENT DOCUMENTS

| | | | |
|---|---|---|---|
| 4,695,662 | 9/1987 | Vora ..................... | 585/324 |
| 4,806,695 | 2/1989 | Vora et al. ............ | 568/697 |
| 4,906,788 | 3/1990 | Scott et al. ........... | 568/697 |

*Primary Examiner*—P. Achutamurthy
*Attorney, Agent, or Firm*—Oblon, Spivak, McClelland, Maier & Neustadt

[57] ABSTRACT

An integrated process for producing iso-butene and alkyl tert-butyl ethers in which the iso-butene is obtained by dehydrogenation of iso-butane followed by purification by partial condensation plus absorption of residual vapor with a solvent, the alkyl tert-butyl ether being obtained by reacting the purified iso-butene product with the corresponding alcohol, the essential characteristic being that the solvent used for absorbing the iso-butene is part of the product alkyl tert-butyl ether itself and/or part of the corresponding alcohol used in the process.

4 Claims, 5 Drawing Sheets

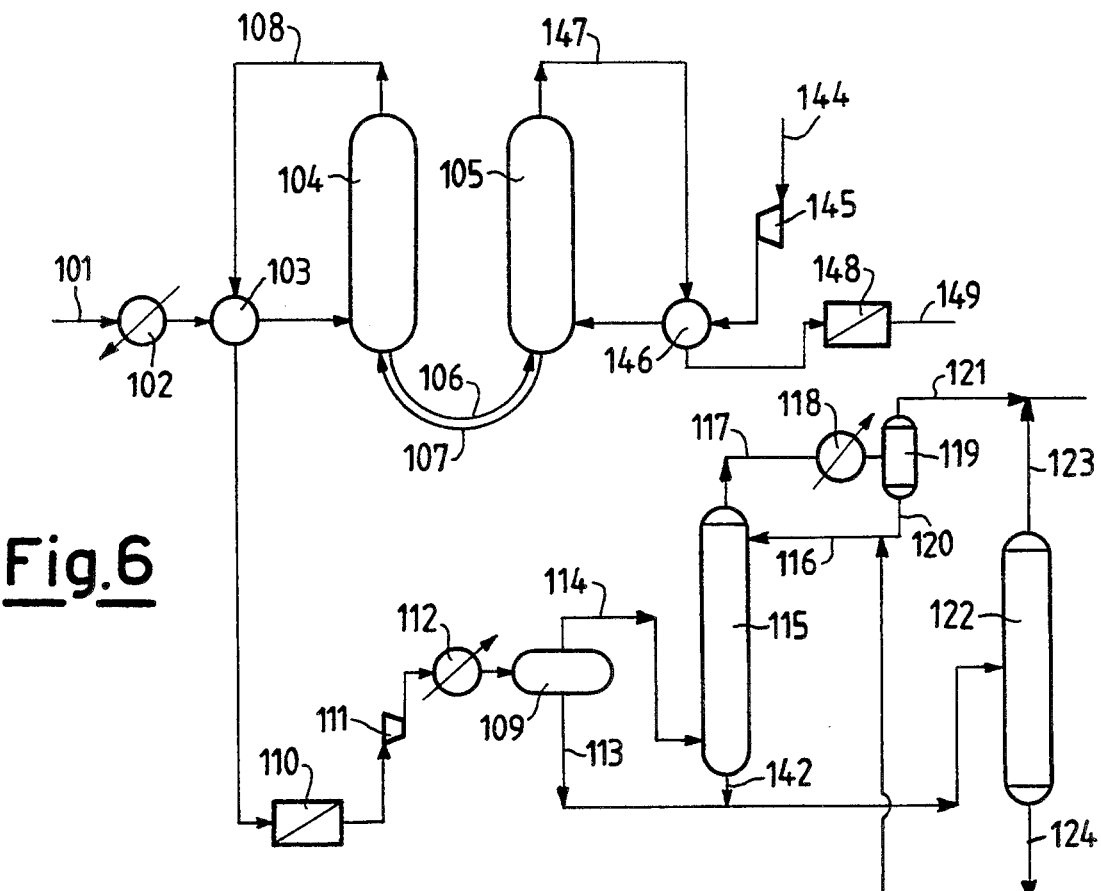
Fig.6
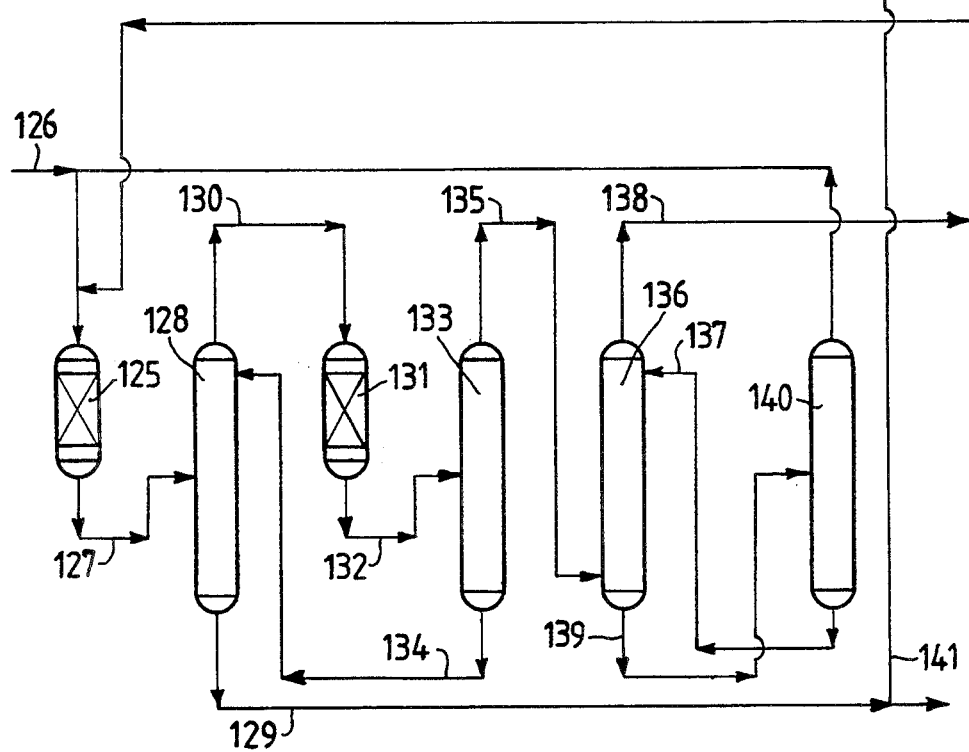

INTEGRATED PROCESS FOR PRODUCING ISO-BUTENE AND ALKYL TERT-BUTYL ETHERS

This is a continuation of application Seq. No. 07/787,790, filed on Nov. 4, 1991, U.S. Pat. No. 5,254,764.

This invention relates to an integrated process for producing iso-butene and alkyl tert-butyl ethers such as methyl tert-butyl ether (MTBE), ethyl tert-butyl ether (ETBE), etc.

Alkyl tert-butyl ethers are used as high-octane additives for gasolines, and are produced by reacting iso-butene with the corresponding alcohol (methanol for MTBE, ethanol for ETBE, etc.) in the liquid phase over a suitable catalyst at a pressure of 15–40 atmospheres and a temperature of 60°–100° C. (see patent IT-1012690).

The current tendency to introduce increasingly higher quantities particularly of MTBE into gasoline technology and the almost complete utilization of refinery streams containing iso-butene has led to the development of complexes for iso-butene production via dehydrogenation of iso-butane.

The raw material is usually a mixture of field butanes, a typical block diagram of an MTBE plant therefore being as shown in FIG. 1.

The feedstock 1 comprising normal and iso-butane is fed into the distillation column 2, from which essentially iso-butane 3 leaves at the top and a stream 4 containing n-$C_4$ and higher hydrocarbons is withdrawn from the bottom. A part 5 of the bottom stream is isomerized in the reactor 6 and recycled through 7 to the column 2.

The iso-butane 3 is dehydrogenated in the plant 8, which provides a light gas stream 9 and a stream 10 containing iso-butane and iso-butene, which is fed to MTBE synthesis 11, in which it reacts with methanol 12 to produce MTBE 13.

In addition to the MTBE, the plant 11 also provides a stream 14 containing iso-butane, which is recycled to a point upstream of the dehydrogenation reactor 8.

It should be noted that the origin of dehydrogenation techniques was unrelated to MTBE production.

However, it is predicted that most new MTBE plants will use iso-butene produced by dehydrogenation of iso-butane and likewise most iso-butane dehydrogenation plants will supply iso-butene to MTBE plants.

Any integration of these two plants which results in savings in investment and/or operating costs is therefore of considerable interest.

The iso-butane dehydrogenation unit, a scheme of which is shown in FIG. 2, is based on a process similar to those currently used commercially, ie gas preparation, compression and purification. More specifically, the iso-butane 21 is fed to the dehydrogenation reactor 22, which is followed by a compression stage 23 and a purification stage 24.

The purification comprises separation of hydrogen, nitrogen and light hydrocarbons 25 from the $C_4$ hydrocarbon component of the reaction product 26.

One of the most problematic points is the recovery of $C_4$ hydrocarbons from the light gas stream which have remained uncondensed after compression.

In current plants this recovery is achieved by cryogenic methods. It can also be achieved by absorption in a suitable solvent followed by $C_4$ stripping and solvent regeneration.

For example, in iso-butane dehydrogenation plants the solvent is a mixture of $C_6$–$C_{10}$ hydrocarbons.

FIG. 3 shows a typical scheme of the Snamprogetti-Yarsintez iso-butane dehydrogenation process with recovery by cryogenic methods (see Octane Week, Oct. 8, 1990, pages 7–8).

The iso-butane 31 is preheated in the heat exchangers 32 and 33 before being fed to the dehydrogenation reactor 34, which is connected to the dehydrogenation catalyst regenerator 35 by the lines 36 and 37.

A gaseous stream 38 leaves the top of the reactor 34 and is fed to the separator 39 after being cooled in 33, filtered in 40, compressed in 41 and partially condensed in 42.

Two streams are obtained from the separator 39, one 43 containing mainly $C_4$ hydrocarbons and the other 44 containing mainly hydrogen and $C_3$ hydrocarbons.

The stream 43 is fed to the depropanizer 45, from the bottom of which a stream 46 consisting essentially of iso-$C_4$ is withdrawn. The stream 44 is fed to a low temperature recovery system 47 to recover the iso-butene and iso-butane 48 contained in it, to be added to the stream 43. The stream 49 leaving 47 and containing essentially hydrogen and $C_1$–$C_3$ hydrocarbons is combined with the stream 50 leaving the top of the depropanizer 45.

Air 51 is fed to the regeneration column 39 after being compressed in 52 and heated in 53.

A gaseous stream 54 leaves the top of the column 39 and is cooled in 53 and filtered through 55 before being used as fuel gas 56. FIG. 4 shows a typical scheme of the iso-butane dehydrogenation process with recovery by absorption and stripping.

Only the part relating to the purification will be described as the remainder is similar to that shown in FIG. 3.

The stream 38 leaving the reactor 34 is cooled in 33, compressed in 41 and partly condensed in the condenser 42 before being fed to the separator 39 to separate heavy hydrocarbons 43 from light hydrocarbons 44, these latter being fed to the absorber 60.

The light gases and hydrocarbons 61 leave the top of said absorber, whereas the remainder is absorbed by the solvent fed through the line 62 and is withdrawn from the bottom 63.

The stream 63 containing the spent solvent and the $C_4$ hydrocarbons is fed to a distillation column 64, from the bottom 65 of which the regenerated solvent is obtained and from the top of which a stream is obtained containing essentially $C_4$ hydrocarbons 66, this being fed to the depropanizer column 67 after being added to the stream 43. A stream consisting essentially of iso-$C_4$ is withdrawn from the bottom 68 of the column 67, and a stream containing essentially $C_3$ hydrocarbons leaves from the top 69.

These recovery procedures are very costly and complicated. In particular, the cryogenic system suffers from high investment and operating costs because of a refrigeration cycle operating at very low temperature and the costly machinery involved (such as turboexpanders).

Recovery by absorption and stripping has the drawback of introducing solvent substances extraneous to the production cycle, which have then to be carefully recovered with resultant increased operating costs and an excessive heavy hydrocarbon enrichment of the $C_4$ fraction. The high utilities consumption in desorbing the $C_4$s from the solvent must also be considered.

It has surprisingly been found possible to recover the C$_4$ hydrocarbons from the vapours originating from the first condensation by absorption in alkyl tert-butyl ether and/or in the corresponding alcohol used, without reducing the yield below that of the aforesaid methods, even though the high vapour pressure of these compounds under the process conditions would seem to discourage its use.

BRIEF DESCRIPTION OF THE DRAWINGS

A more complete appreciation of the invention and many of the attendant advantages thereof, will be readily obtained as the same becomes better understood by reference to the following detailed description when considered in connection with the accompanying drawings, wherein:

FIG. 6 shows an integrated process scheme for producing MTBE using MTBE as absorbent.

Figure 1:
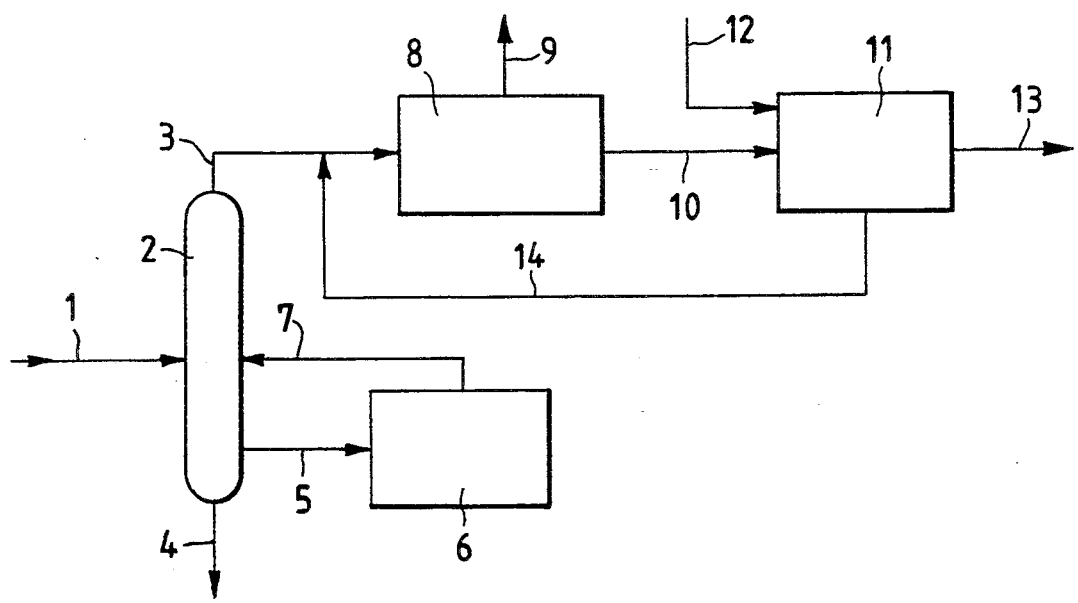
FIG. 1 shows a typical block diagram of an MTBE plant.
Figure 2:
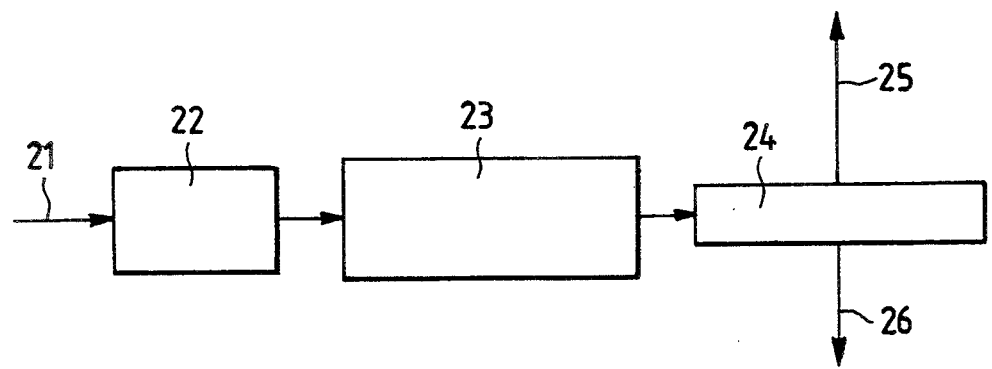
FIG. 2 shows an iso-butane dehydrogenation unit.
Figure 3:
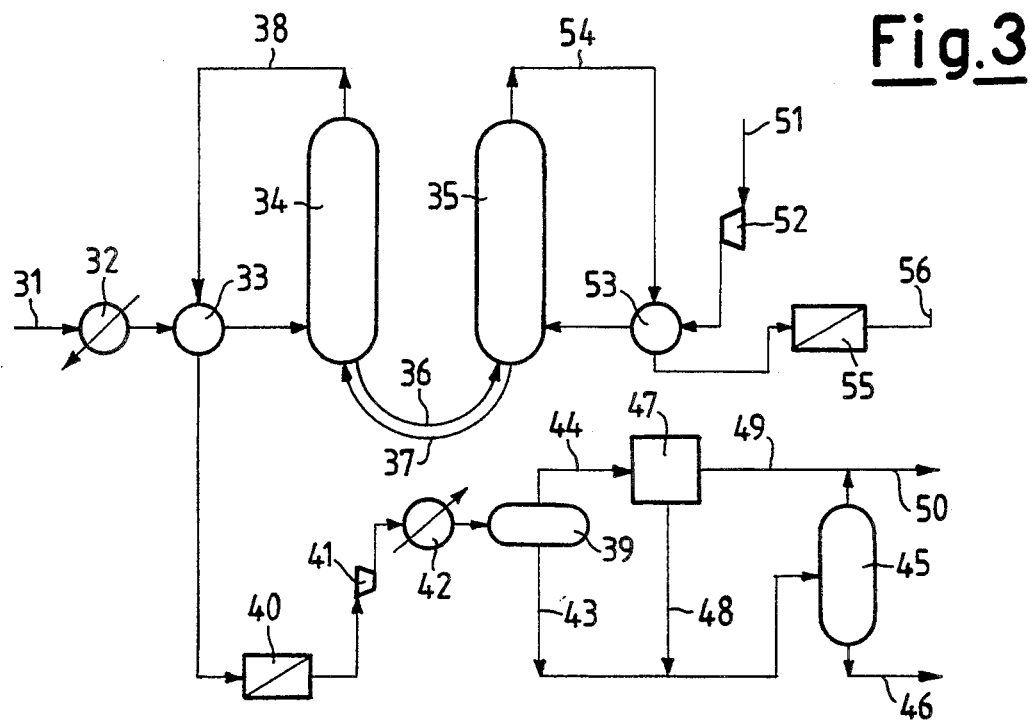
FIG. 3 shows a typical scheme of the Snamprogetti-Yarsintez iso-butane dehydrogenation process.
Figure 4:
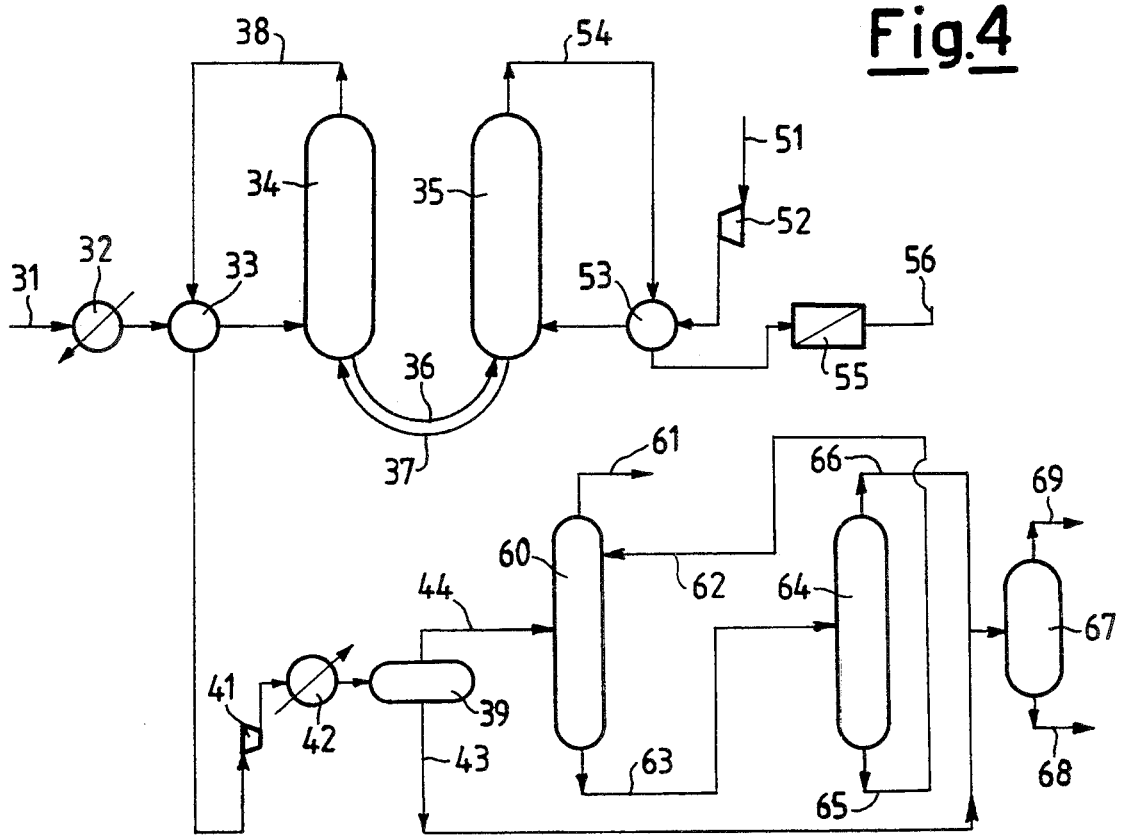
FIG. 4 shows a process using absorption in heavy hydrocarbons.

Compared with absorption in heavy hydrocarbons, as applied in the process illustrated in FIG. 4, the main advantage of the use of these solvents is that the compounds are present as reagents (methanol, ethanol, etc.) or as products (MTBE, ETBE etc.) and that the streams containing the recovered C$_4$s and solvent can be fed directly to process units already provided in the alkyl tert-butyl ether production plant without undergoing further treatment. Considering the universally used cryogenic scheme it is also apparent that a system operating at very low temperature is more complicated than an absorption column operating at a temperature of 40°–60° C.

The integrated process for producing iso-butene and alkyl tert-butyl ether according to the present invention comprises essentially the following stages:

a) dehydrogenating a stream containing iso-butane, then compressing and partially condensing the gases produced to obtain, after separation, a gaseous stream containing hydrogen, nitrogen and C$_1$–C$_4$ hydrocarbons and a liquid stream containing mainly C$_4$ hydrocarbons;

b) feeding the gaseous stream to an absorption column employing solvent to obtain from the top a gaseous mixture containing essentially hydrogen, nitrogen and C$_1$–C$_3$ hydrocarbons and from the bottom a liquid mixture containing essentially C$_4$ hydrocarbons and the spent solvent;

c) feeding the liquid stream containing mainly C$_4$ hydrocarbons to a distillation column to obtain from the top a gaseous mixture containing essentially C$_3$ hydrocarbons and from the bottom a liquid mixture containing iso-butane and iso-butene;

d) feeding the liquid mixture containing iso-butane and iso-butene of stage c) to a reactor, or to a first reactor if two or more reactors are used, together with the corresponding alcohol to obtain the alkyl tert-butyl ether;

e) feeding the product from the reactor to a distillation column to obtain from the top a stream containing mainly the unreacted gases from the bottom a liquid containing essentially alkyl tert-butyl ether;

f) feeding the stream containing mainly unreacted gases of stage e) directly to a wash column if only one reactor is used, or to the second reactor if two or more reactors are used, then feeding the product from said second reactor to a distillation column to obtain from the bottom a liquid mixture containing alkyl tert-butyl ether, which is recycled to the distillation column of stage e) or to a third reactor if several reactors are used, and from the top a mixture containing mainly unreacted gases, this stream being fed to a wash column;

g) separation in the wash column to obtain from the top essentially the unreacted C$_4$ hydrocarbons and from the bottom a liquid mixture containing essentially water and the alcohol used, these then being separated in a distillation column, characterised in that the solvent used in the absorption column of stage b) is part of the liquid containing essentially the alkyl tert-butyl ether of stage e) and/or part of the corresponding alcohol used in the process.

The liquid mixture containing essentially C$_4$ hydrocarbons and the alkyl tert-butyl ether as spent solvent leaving the bottom of the absorption column of stage b) can be fed partly or totally to one or more of the following equipment items:

to the distillation column of stage c);
to the distillation column of stage e);
to the reactor of stage d).

It should be noted that it is not necessary to regenerate the alkyl tert-butyl ether as said liquid mixture is not necessarily fed to the distillation column of stage c).

If the corresponding alcohol used in the process is also used as solvent in the absorption column of stage b), the liquid mixture leaving the column is fed to the reactor of stage d).

The alcohol separated in the distillation column downstream of the wash column of stage g) can be recycled to the reactor of stage d), and/or to the reactor of stage f) if two or more reactors are used, and/or to the absorption column of stage b).

The unreacted C$_4$ hydrocarbons separated in the wash column of stage g) can be conveniently mixed with the stream containing iso-butane of stage a) to be dehydrogenated together.

The aforedescribed process can also be conducted using a column reactor in which the reactor and distillation column are combined into one and the same equipment item. In this case, part of the liquid containing essentially alkyl tert-butyl ether directly leaving the column reactor is recycled to the absorption column of stage b).

The quantity of solvent used in the absorption column of stage b) preferably lies within the following ranges:

for the alkyl tert-butyl ether as sole solvent, from 0.5 to 2 moles/mole of C$_4$ hydrocarbon contained in the absorption column, and more preferably from 1 to 1.5;

for the corresponding alcohol as sole solvent, from 1 to 3 moles/mole of C$_4$ hydrocarbon contained in the absorption column, and more preferably from 1.5 to 2.

In the case of mixed solvent, the quantities of the alkyl tert-butyl ether and the corresponding alcohol can be obviously reduced below the above specified ratios.

When the alkyl tert-butyl ether is used alone as solvent, that part of the liquid containing it to be fed to the absorption column is preferably between 15 and 50% by volume, and more preferably between 30 and 45%, of the total liquid leaving the distillation column of stage e).

The invention will be more apparent from the accompanying figures which show some preferred but non-limiting examples thereof.

Figure 5:
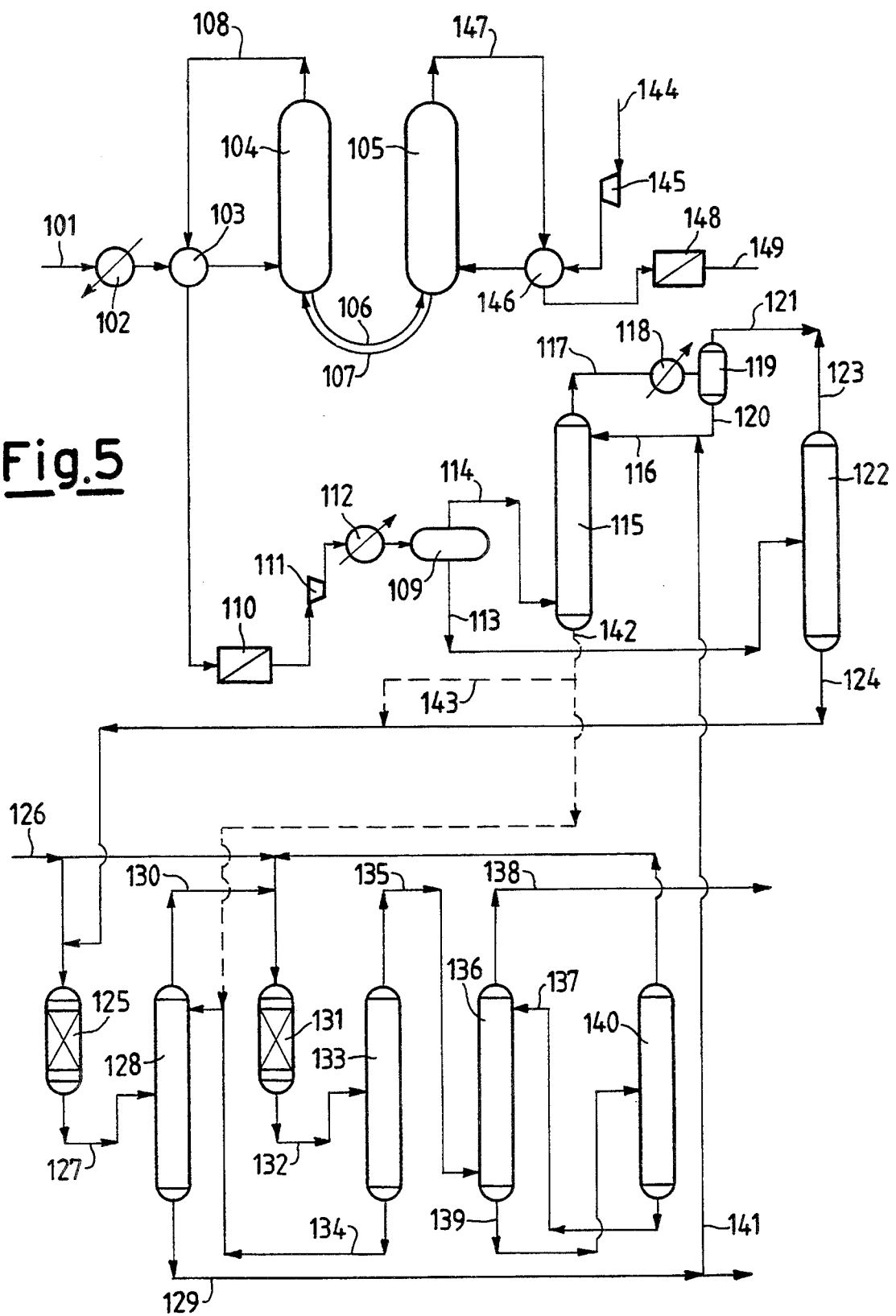
FIG. 5 shows an integrated process scheme for producing MTBE.

FIG. 5 shows an integrated process scheme for producing MTBE, using MTBE as absorbent.

The feedstock 101 containing normal and iso-butanes is preheated in the heat exchangers 102 and 103 before being fed into the dehydrogenation reactor 104 which is connected to the dehydrogenation catalyst regenerator 105 by the lines 106 and 107. A gaseous stream 108 leaves the top of the reactor 104 and is fed to the separator 109 after being cooled in 103, filtered through 110, compressed in 111 and partly condensed in 112, to separate the heavy hydrocarbons 113 from the lighter hydrocarbons 114 which are fed to the absorber 115 in which MTBE 116 is used as solvent. The light gases 117 leaving the top of the absorber 115 are cooled in 118 and separated in 119 to separate from the gases 121 the MTBE 120, which is recycled to the absorber.

The liquid stream 113 is fed to a distillation column 122 to obtain $C_3$ hydrocarbons from the top 123 and iso-butene and iso-butane from the bottom 124.

The iso-$C_4$s 124 are fed to a first reactor 125 together with methanol 126 to obtain a stream containing MTBE 127, which is fed to a distillation column 128 to obtain the desired MTBE 129 from the bottom and the unreacted gases (methanol, iso-butene and iso-butane) 130 from the top.

The gaseous stream 130 is fed into a second reactor 131 together with methanol to obtain a further stream containing MTBE 132 (with a lesser MTBE content than the stream 127), which is fed into a distillation column 133, from the bottom of which a stream 134 is obtained containing essentially MTBE which is recycled to the column 128, and from the top of which a stream 135 is obtained containing methanol, iso-butane and iso-butene, which is fed to a wash column 136 into which water 137 is fed.

Iso-butane 138 leaves the top of the column 136 to be recycled by being added to the stream 101, and methanol and water 139 leave the bottom to be separated in the column 140.

A part of the stream 129 containing essentially MTBE is recycled 141 as solvent to the absorption column 115. The liquid stream 142 containing the $C_4$ hydrocarbons and MTBE is fed to the distillation column 128. Part or all of it could however be fed via 143 to the reactor 125.

Air 144 is fed to the regeneration column 105 after being compressed in 145 and heated in 146. A gaseous stream 147 leaves the top of the column 105 and is cooled in 146 and filtered in 148 before being used as fuel gas 149.

FIG. 6 shows a possible integrated process scheme for producing MTBE using MTBE as absorbent, as in the scheme of FIG. 5, but with the difference that the bottom stream from the absorber 142 is fed together with the liquid 113 from the separator 109 to the distillation column 122.

In this manner the $C_3$ hydrocarbons partially absorbed by the solvent are further removed.

The reference numerals on the scheme of FIG. 6 have the same meaning as those of FIG. 5.

Figure 7:
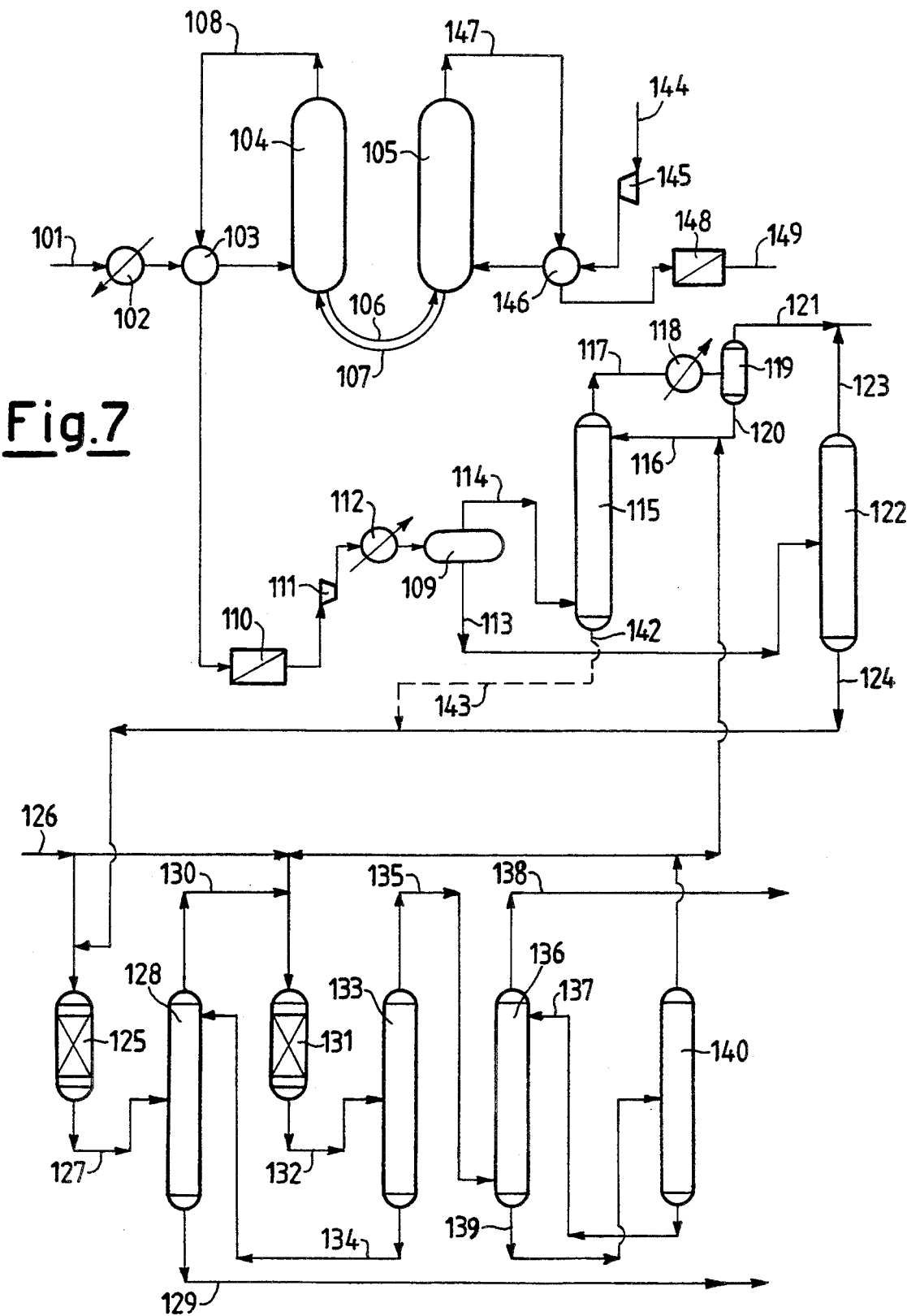
FIG. 7 shows an integrated scheme for producing MTBE using methanol as absorbent.

FIG. 7 shows a possible integrated process scheme for producing MTBE using methanol as absorbent. The difference between this and the scheme of FIG. 5 is that part of the methanol is fed to the absorption column 115 instead of part of the MTBE, the reference numerals having the same meaning as in FIG. 5.

Two examples are given hereinafter to better illustrate the invention.

EXAMPLE 1

100 kmol/h of iso-butane are fed to a dehydrogenation reactor operating in the gaseous phase at a temperature of 580° C. and at atmospheric pressure, with a Cr—Al catalyst.

The reactor effluent consists of:
52.0 kmol/h of iso-butane
43.9 kmol/h of iso-butene
49.0 kmol/h of hydrogen
3.8 kmol/h of methane
2.3 kmol/h of $C_3$ hydrocarbons
1.5 kmol/h of $C_5$ and higher hydrocarbons The reactor effluent is compressed to 20 atmospheres and cooled to 40° C. to separate into a liquid stream and a gaseous stream. The liquid stream is formed essentially of $C_3$, $C_4$ and higher hydrocarbons.

The gaseous stream still contains about 25% of $C_4$ hydrocarbons and has the following composition:
12.2 kmol/h of iso-butane
9.4 kmol/h of iso-butene
47.7 kmol/h of hydrogen
3.4 kmol/h of methane
1.0 kmol/h of $C_3$ hydrocarbons This stream is fed to the bottom of an absorption column, to the top of which liquid MTBE is fed at 35° C. in such a quantity that the molar ratio of MTBE to feed $C_4$ hydrocarbons is 1:1. The column temperature is maintained between 35° and 60° C. In this manner 99.6% of the iso-butene and iso-butene contained in the feed is recovered, with 0.5% of the solvent being lost with the overhead vapour stream.

The bottom liquid stream has the following composition:
12.15 kmol/h of iso-butane
9.36 kmol/h of iso-butene
0.65 kmol/h of hydrogen
0.20 kmol/h of methane
0.62 kmol/h of $C_3$ hydrocarbons
21.49 kmol/h of MTBE This stream is mixed with the liquid stream from the condensation at 40° C., to give the following stream:
51.95 kmol/h of iso-butane
43.86 kmol/h of iso-butene
1.95 kmol/h of hydrogen
0.60 kmol/h of methane
1.92 kmol/h of $C_3$ hydrocarbons
1.50 kmol/h of $C_5$ and higher hydrocarbons
21.49 kmol/h of MTBE This mixture is fed to a distillation column from which a residue is recovered containing the MTBE, the $C_4$ hydrocarbons and a small quantity of propane and propylene.

This residue is mixed with methanol in a quantity such that the methanol/iso-butene ratio is 1:1, and fed at an LHSV of 5 into the primary reactor for MTBE synthesis, where it reacts on Amberlyst 15 resin at a temperature of 60° C. and a pressure of 15 atg. The following stream leaves the reactor:
- 51.95 kmol/h of iso-butane
- 5.48 kmol/h of iso-butene
- 5.48 kmol/h of methanol
- 0.42 kmol/h of $C_3$ hydrocarbons
- 1.50 kmol/h of $C_5$ and higher hydrocarbons
- 59.87 kmol/h of MTBE This stream is fed to the fractionation column to obtain MTBE at 98% purity from the bottom and from the top a liquid distillate which is fed to the second reactor after methanol has been added to the extent that the methanol/iso-butene molar ratio is 1.3:1. Again operating on Amberlyst 15 at 60° C. and at an LHSV of 5, the following effluent is obtained:
- 51.95 kmol/h of iso-butane
- 0.60 kmol/h of iso-butene
- 2.24 kmol/h of methanol
- 0.42 kmol/h of $C_3$ hydrocarbons
- 4.88 kmol/h of MTBE Hence although having fed MTBE to the first reactor, a yield of 98.4% on the iso-butene feed is obtained.

EXAMPLE 2

This is identical to Example 1 as far as the feed to the absorption column.

In this case methanol is used as solvent, in a ratio of 1.5:1 to the $C_4$ hydrocarbons.

98% of the iso-butane and 99.5% of the iso-butene are recovered, losing 0.1% of the solvent.

The liquid stream leaving the bottom of the absorber has the following composition:
- 12.02 kmol/h of iso-butane
- 9.35 kmol/h of iso-butene
- 32.37 kmol/h of methanol
- 0.25 kmol/h of hydrogen
- 0.35 kmol/h of methane
- 0.65 kmol/h $C_3$ of hydrocarbons This stream is mixed with the residue of the light hydrocarbon separation fractionation column fed with the liquid stream condensed at 40° C. after compression, and after being degassed and mixed with methanol to a methanol/iso-butene molar ratio of 1:1 is fed to the first MTBE synthesis reactor operating under the conditions of Example 1.

In this case, without feeding the product to the MTBE plant an overall yield of 99% on the iso-butene feed is obtained.

We claim:

1. An integrated process for producing iso-butene and tert-butyl methyl ether or tert-butyl ethyl ether, comprising:
   a) dehydrogenating a stream containing iso-butane, then compressing and partially condensing the gases produced to obtain, after separation, a gaseous stream containing hydrogen, nitrogen and $C_1$–$C_4$ hydrocarbons, and a liquid stream containing mainly $C_4$ hydrocarbons;
   b) feeding said gaseous stream to an absorption column employing solvent to obtain from the top a gaseous mixture containing essentially hydrogen, nitrogen and $C_1$–$C_3$ hydrocarbons and from the bottom a liquid mixture containing essentially $C_4$ hydrocarbons and the spent solvent;
   c) feeding said liquid stream containing mainly $C_4$ hydrocarbons to a distillation column to obtain from the top a gaseous mixture containing essentially $C_3$ hydrocarbons and from the bottom a liquid mixture containing iso-butane and iso-butene;
   d) feeding the liquid mixture containing iso-butane and iso-butene from stage c) to a reactor, or to a first reactor if two or more reactors are used, together with methanol or ethanol to obtain the tert-butyl methyl ether or tert-butyl ethyl ether;
   e) feeding the product from the reactor to a distillation column to obtain from the top a stream containing mainly the unreacted gases and from the bottom a liquid containing essentially tert-butyl methyl ether or tert-butyl ethyl ether;
   f) feeding the stream containing mainly unreacted gases from stage e) directly to a wash column if only one reactor is used, or to a second reactor if two or more reactors are used, then feeding the product from said second reactor to a distillation column to obtain from the bottom a liquid mixture containing tert-butyl methyl ether or tert-butyl ethyl ether, which is recycled to the distillation column of stage e), or to a third reactor if several reactors are used, and from the top a mixture containing mainly unreacted gases, this stream being fed to a wash column; and
   g) separation in the wash column to obtain from the top essentially the unreacted $C_4$ hydrocarbons and from the bottom a liquid mixture containing essentially water and methanol or ethanol used, these then being separated in a distillation column, wherein the solvent used in the column stage b) is a fraction of methanol or ethanol which is used in the process which additionally comprises tert-butyl methyl ether or tert-butyl ethyl ether.

2. A process as claimed in claim 1, wherein the alcohol separated in the distillation column downstream of the wash column of stage g) is recycled to the reactor of stage d), and/or, if two or more reactors are used, to the reactor of stage f), and/or to the absorption column of stage b).

3. A process as claimed in claim 1, wherein the unreacted $C_4$ hydrocarbons separated in the wash column of stage g) are mixed with the stream containing iso-butane of stage a).

4. An integrated process for producing iso-butene and tert-butyl methyl ether or tert-butyl ethyl ether, comprising:
   a) dehydrogenating a stream containing iso-butane, then compressing and partially condensing the gases produced to obtain, after separation, a gaseous stream containing hydrogen and $C_1$–$C_4$ hydrocarbons, and a liquid stream containing mainly $C_4$ hydrocarbons;
   b) feeding said gaseous stream to an absorption column employing solvent to obtain from the top a gaseous mixture containing essentially hydrogen and $C_1$–$C_3$ hydrocarbons and from the bottom a liquid mixture containing essentially $C_4$ hydrocarbons and the spent solvent;
   c) feeding said liquid stream containing mainly $C_4$ hydrocarbons to a distillation column to obtain from the top a gaseous mixture containing essentially $C_3$ hydrocarbons and from the bottom a liquid mixture containing iso-butane and iso-butene;
   d) feeding the liquid mixture containing iso-butane and iso-butene from stage c) to a reactor, or to a first reactor if two or more reactors are used, together with methanol or ethanol to obtain the tert-butyl methyl ether or tert-butyl ethyl ether;

e) feeding the product from the reactor to a distillation column to obtain from the top a stream containing mainly the unreacted gases and from the bottom a liquid containing essentially tert-butyl methyl ether or tert-butyl ethyl ether;

f) feeding the stream containing mainly unreacted gases from stage e) directly to a wash column if only one reactor is used, or to a second reactor if two or more reactors are used, then feeding the product from said second reactor to a distillation column to obtain from the bottom a liquid mixture containing tert-butyl methyl ether or tert-butyl ethyl ether, which is recycled to the distillation column of stage e), or to a third reactor if several reactors are used, and from the top a mixture containing mainly unreacted gases, this stream being fed to a wash column; and g) separation in the wash column to obtain from the top essentially the unreacted $C_4$ hydrocarbons and from the bottom a liquid mixture containing essentially water and methanol or ethanol used, these then being separated in a distillation column, wherein the solvent used in the column stage b) is a fraction of methanol or ethanol which is used in the process.

\* \* \* \* \*

UNITED STATES PATENT AND TRADEMARK OFFICE
CERTIFICATE OF CORRECTION

PATENT NO. : 5,446,224
DATED : August 29, 1995
INVENTOR(S) : Ivano MIRACCA, et al.

It is certified that error appears in the above-indentified patent and that said Letters Patent is hereby corrected as shown below:

On the title page, Item [73], the Assignee should read:

--Snamprogetti S.p.A., Milan, Italy--

Signed and Sealed this

Second Day of January, 1996

Attest:

BRUCE LEHMAN

Attesting Officer      *Commissioner of Patents and Trademarks*